United States Patent [19]

Nierlich et al.

[11] Patent Number: 5,177,282
[45] Date of Patent: Jan. 5, 1993

[54] OLIGOMERIZATION OF OLEFINS

[75] Inventors: Franz Nierlich; Joachim Neumeister, both of Marl; Thomas Wildt, Haltern; Wilhelm Droste; Fritz Obenaus, both of Marl, all of Fed. Rep. of Germany

[73] Assignee: Huels Aktiengesellschaft, Marl, Fed. Rep. of Germany

[21] Appl. No.: 503,951

[22] Filed: Apr. 4, 1990

[30] Foreign Application Priority Data

May 5, 1989 [DE] Fed. Rep. of Germany ....... 3914817

[51] Int. Cl.$^5$ ................................................. C07C 1/00
[52] U.S. Cl. .................................. 585/329; 585/518; 585/519; 585/531
[58] Field of Search ................ 585/329, 518, 519, 531

[56] References Cited

U.S. PATENT DOCUMENTS

| 2,828,347 | 3/1958 | Hogan et al. | |
|---|---|---|---|
| 2,906,790 | 9/1959 | Smyth et al. | |
| 3,080,433 | 3/1963 | Hengstebeck | 585/824 |
| 3,221,073 | 11/1965 | Davis et al. | 585/855 |
| 3,242,641 | 3/1966 | Makin | 55/33 |
| 3,402,217 | 9/1968 | Engelbrecht, et al. | 585/510 |
| 3,662,015 | 5/1972 | Komatsu et al. | 585/261 |
| 3,816,975 | 6/1974 | Collins | |
| 4,538,012 | 8/1985 | Miller | 585/255 |
| 4,608,450 | 8/1986 | Miller | 585/517 |
| 4,717,782 | 1/1988 | Garwood et al. | 585/531 |

FOREIGN PATENT DOCUMENTS

| 0133052 | 7/1984 | European Pat. Off. |
| 0229994 | 12/1986 | European Pat. Off. |
| 0281208 | 3/1988 | European Pat. Off. |
| 281208 | 9/1988 | European Pat. Off. |
| 2154603 | 9/1985 | United Kingdom |

OTHER PUBLICATIONS

O. W. Litwin "Osnowy Technologii Sintesa Kautschuka" (=Grundlagen der Technologie der Kautschuksynthese), Verlag "Chimija", Moskau 1972, Seiten 136–138 (Kopie Anbei).

Tsch. Tomas "Promyschlennye Katalititscheski Prozessy I Effektiwnye Katalisatory" (=Industrielle Katalytische Prozesse und Wirksame Katalysatoren), Verlag "Mir", 1973, Seite 189 (Kopie Anbei).

Primary Examiner—Patrick P. Garvin
Assistant Examiner—E. D. Irzinski
Attorney, Agent, or Firm—Oblon, Spivak, McClelland, Maier & Neustadt

[57] ABSTRACT

Olefins are oligomerized by passing a hydrocarbon feedstock mixture containing olefins of from 2 to 8 carbon atoms over a molecular sieve having a pore diameter of from greater than 4 angstroms to 15 angstroms, and then oligomerizing said olefins by passing the hydrocarbon feedstock over a nickel-containing catalyst at a temperature of from 0° to 200° C. and at a pressure of from 1 to 70 bar absolute.

12 Claims, No Drawings

OLIGOMERIZATION OF OLEFINS

BACKGROUND OF THE INVENTION

1. Field of the Invention

The present invention relates to a process for oligomerizing olefins of from 2 to 8 carbon atoms or mixtures over a nickel-containing catalyst at temperatures of from 0° to 200° C. and pressures of from 1 to 70 bar absolute.

2. Description of the Background

Olefins of from 2 to 8 carbon atoms or mixtures thereof, in particular olefins of from 2 to 5 carbon atoms, are available in large quantities from refinery crackers, and therefore are important raw materials for the entire petrochemical industry. For instance, polymers of ethylene, propylene and 1-butylene or mixtures thereof have found numerous applications.

Equally, however, the branched oligomers of olefins of from 2 to 8 carbon atoms, prepared by acid catalysis, have become important in industry. For instance, polymer gasoline has been produced from $C_3/C_4$-olefin mixtures for decades, and various fractions isolated from polymer gasoline are used as starting materials, for example for PVC plasticizers and detergents.

The importance of petrochemical products produced from polymer gasoline fractions is exceeded by that of products produced from more linear olefin oligomers because, for example, such detergents or detergent bases are more biodegradable or because such PVC plasticizers have inter alia lower viscosities and improved low temperature properties, yet a similar vapor pressure. Less branched oligomers of from 10 to 16 carbon atoms produced from $C_5/C_6$-olefin cuts are highly suitable for use as diesel motor fuel component. This aspect is of great importance in those countries where the motor fuel supply is chiefly based on coal.

The more linear oligomers of lower olefins are obtainable by reacting the latter at temperatures of about 0°–200° C. and pressures of about 1–70 bar not only over homogeneous, but also over heterogeneous catalysts, when the active component is predominantly nickel. However, there are other possible catalytically active metals, for example ruthenium (G. Braca, G. Slzana; La Chimica e l'Industria, 56 (1974), 110–116), palladium, as disclosed in U.S. Pat. No. 4,436,946, and copper, cobalt, iron, chromium and titanium as disclosed in GB Patent 824,002. However, only the nickel-containing catalysts have become industrially important.

DE Patent 2,855,423 discloses a homogeneous catalyst system consisting of the nickel(II) salt of octanoic acid, ethylaluminum dichloride and a free fatty acid. A catalyst system of this kind is also used in the only homogeneously catalyzed olefin oligomerization process of industrial importance (DIMERSOL ®) (Y. Chauvin et al., Chemistry and Industry, 1974, 375–378). Homogeneously catalyzed processes for oligomerizing olefins are very cost-intensive because of the technically complicated process of removing the catalyst system and, what is more, it is necessary to provide for a complicated disposal system for the inevitable waste product formed in the course of the destruction of the catalyst.

Besides homogeneous catalysts the prior art also discloses numerous heterogeneous catalysts based on nickel and silicon which frequently contain aluminum in addition and are prepared in various ways. DD Patent 160,037, for example, discloses the preparation of an Ni/Al precipitation catalyst on $SiO_2$ as carrier material. Other catalysts are obtained by exchanging the positively charged particles, such as protons or sodium ions, present on the carrier surface for nickel ions. A wide variety of different carrier materials are used in the catalysts, for example, amorphous aluminum silicate according to R. Espinoza et al Appl. Cat. 31 (1987), 259–266, crystalline aluminum silicate according to DE Patent 2,029,624, zeolites of the ZSM type according to NL Patent 8,500,459, an X zeolite according to DE Patent 2,347,235, X- and Y-zeolites according to A. Barth et al., Z. Anorg. Allg. Chem. 521 (1985), 207–214, and a mordenite according to EP-A-0,233,302.

It is known that nickel-containing catalysts are sensitive to a wide range of catalyst poisons. Such catalyst poisons are inter alia polyunsaturated hydrocarbons, for example, propyne or butadiene, halogen compounds, oxygen compounds, e.g. water or alcohols, sulfur compounds, e.g. hydrogen sulfide, carbon oxysulfide, thioalcohols and thioethers, and also nitrogen compounds, for example, amines present in the FCC $C_4$-hydrocarbon cut (FCC is the abbreviation for fluid catalytic cracker), or traces of butadiene-extracting agents, e.g. acetonitrile or N-methylpyrrolidone in SC raffinate I (SC being the abbreviation for steam cracker). The mechanism of these catalyst poisons, however, is not well known, but it is suspected that their effect results from the fact that they are more strongly adsorbed on the catalytically active centers than the olefins to be oligomerized. The presence of such catalyst poisons in the olefins to be oligomerized gradually reduces the activity of the catalyst.

Consequently, processes are known in which various compounds are removed from a hydrocarbon mixture. According to DE Patent 2,057,269, prior to the oligomerization, polyenes are preferably catalytically hydrogenated to the corresponding monoolefins to an extent of up to 75%. U.S. Pat. No. 4,153,638 teaches that, after catalytic hydrogenation, the diolefin content should be below 1% by weight. Since the nickel-containing oligomerization catalysts, in general, also show hydrogenation activity, it is possible according to EP Patent 0,091,232, to convert the diolefins into the corresponding olefins by passing the hydrogen-saturated hydrocarbon feedstock mixture over the oligomerization catalyst.

According to U.S. Pat. No. 4,153,638, any dissolved water present in the hydrocarbon feedstock mixture can be removed down to levels of less than 10 ppm by weight by means of customary drying agents, for example, a molecular sieve having a pore diameter of 3 angstroms or activated bauxite. Other high-boiling oxygen compounds are removed according to DE Patent 2,057,269 as the bottom product in a distillation of the hydrocarbon mixture.

Sulfur compounds can be removed by an alkali wash, and nitrogen compounds by a water wash, the preference of U.S. Pat. No. 4,153,638 being hydrocarbon oligomerization mixtures containing less than 1 ppm by weight of sulfur and 0.3 ppm by weight of nitrogen. However, the prior art processes do not achieve a thorough removal of such compounds. For instance, a refinery-produced propene/propane mixture (about 75% by weight of propene and about 25% by weight of propane) still contains, even after desulfurization of high-boiling sulfur compounds, for example, dimethyl sulfide (boiling point: 38° C.) or dimethyl disulfide (boiling point: 109° C.), in concentrations of less than 0.5 ppm by weight. However, these levels of sulfur compounds are sufficient to shorten the lifetime of the oligomerization catalyst to the point of the process becoming uneconomical.

A further example are $C_4$-hydrocarbon cuts which, despite prior distillation may still contain trace amounts of high-boiling oxygen compounds, for example methyl tert-butyl ether, tert-butyl alcohol and acetone. The same is true of $C_5$-hydrocarbon cuts, for example pyrolysis gasoline. Since, however, catalyst poisons are effective even in trace amounts, the abovementioned prior art rough purification processes are not sufficient to ensure the removal of catalyst from the hydrocarbon feedstock mixture for the oligomerization of olefins. For this reason and the consequent too short catalyst lifetime, the catalytic processes for oligomerizing olefins, in particular the heterogeneously catalyzed processes, have failed to become established in practice.

SUMMARY OF THE INVENTION

Accordingly, one object of the present invention is to provide a more economical process for oligomerizing olefins wherein any catalyst poisons are removed to such an extent from the hydrocarbon feedstock mixture prior to oligomerization that the nickel-containing catalyst has a long lifetime.

Accordingly, this object and other objects of the present invention as hereinafter will become more readily apparent can be attained in a process of oligomerizing olefins by passing the hydrocarbon feedstock mixture containing olefins of from 2 to 8 carbon atoms over a molecular sieve having a pore diameter of from greater than 4 angstroms to 15 angstroms; and then oligomerizing said olefins by passing the hydrocarbon feedstock over a nickel-containing catalyst at a temperature of from 0° to 200° C. and at a pressure of from 1 to 70 bar absolute.

DETAILED DESCRIPTION OF THE PREFERRED EMBODIMENTS

It has now been found that if a hydrocarbon feedstock mixture is passed over a molecular sieve having a pore diameter of from greater than 4 angstroms to 15 angstroms the lifetime of the nickel-containing catalyst employed in oligomerization is prolonged to such an extent that even the industrial use of the catalytic process for oligomerizing olefins is now an economic proposition.

The olefins in a given hydrocarbon feedstock mixture can be oligomerized not only over a homogeneous, but also over a heterogeneous nickel-containing catalyst. Preferably olefins are oligomerized over a heterogeneous nickel-containing catalyst, particularly preferably over a nickel-containing fixed-bed catalyst and most preferably over a nickel-, silicon- and aluminium-containing fixed-bed catalyst. Furthermore, the olefins in the hydrocarbon feedstock mixture can be oligomerized in the liquid phase, in the gas-liquid mixed phase or in the gas phase. Preferably they are oligomerized in the liquid phase.

Suitable molecular sieves useful in the process of the invention include not only crystalline, natural aluminum silicates, for example phyllo silicates, but also synthetic ones. The process according to the present invention can also be performed using commercial molecular sieves, for example products from Bayer AG, Dow, Union Carbide, Laporte or Mobil. These molecular sieves include, for example, zeolites of the A-, X- and Y-type.

It is also possible to use synthetic molecular sieves which besides silicon and aluminum as main constituents contain other atoms as secondary constituents. These elements can be incorporated, for example, into the zeolite by ion exchange with the exchangeable cations. Examples are the exchange with rare earths, for example gallium, indium or lanthanum, or with nickel, cobalt, copper, zinc or silver.

In addition, it is also possible to use in the process of the present invention synthetic zeolites in which other atoms, for example boron or phosphorus, have been incorporated into the lattice by coprecipitation.

Although in principle of no significance, the concentration of the catalyst poisons to be removed does have economic significance, since their concentration determines the volume of molecular sieve to be used in the present process per unit time. Normally, it is favorable to use prior art agents to reduce the catalyst poisons down to about 1000 ppm by weight and then to pass the reduced catalyst poison content hydrocarbon feedstock mixture thus obtained over the molecular sieve of the present invention. For this reason, it is preferable to remove essentially water, alcohols, nitrogen compounds, sulfur compounds and halogen compounds from the hydrocarbon feedstock mixture before it is passed over the molecular sieve having a pore diameter of from greater than 4 angstroms to 15 angstroms.

In this embodiment, the rough removal of water and/or methanol from the hydrocarbon feedstock mixture can preferably be effected with the aid of a molecular sieve having a pore diameter of up to 4 angstroms. An alternative is to remove water and/or methanol and/or ethanol from the hydrocarbon feedstock mixture by azeotropic distillation. The latter option is particularly suitable for hydrocarbon feedstock mixtures from a methyl tertiary-butyl ether plant or a tertiary-amyl methyl ether plant, since dimethyl ether, a by-product of the synthesis of the aforementioned ethers, can be separated at the same time during the course of the azeotropic distillation. If polyunsaturated hydrocarbons are present in the hydrocarbon feedstock mixture, they must be removed therefrom prior to oligomerization. They are preferably removed from the hydrocarbon feedstock mixture by selective hydrogenation, for example as described in EP Patent 81,041 and DE Patent 1,568,542, particularly preferably by a selective hydrogenation down to a residual level of less than 5 ppm by weight. The polyunsaturated hydrocarbons can be removed from the hydrocarbon feedstock mixture not only before the mixture is passed over the molecular sieve to be used according to the present invention but also afterwards.

Quantitative predictions about the efficiency of removal of catalyst poisons from the hydrocarbon feedstock mixture over the molecular sieve employed in the present process are very difficult because frequently the nature of the catalyst poisons is not known. Preferably, the hydrocarbon feedstock mixture is passed prior to the oligomerization over a molecular sieve having a pore diameter of from 7 to 13 angstroms.

In some instances it can also be advantageous for economic reasons to employ two or more of the molecular sieves to be used according to the present invention in series. It is thus also possible to pass the hydrocarbon feedstock mixture prior to the oligomerization over two or more successive molecular sieves having a pore diameter of from greater than 4 angstroms to 15 angstroms. The passing of the hydrocarbon feedstock mixture over the molecular sieve employed in the present invention can be carried out both in the gas phase and in the liquid phase and also in the gas-liquid mixed phase. The weight hourly space velocity (WHSV) preferably ranges from 0.05 to 100 l/h, particularly preferably from 1 to 40 l/h.

The hydrocarbon feedstock mixture is preferably passed, prior to the oligomerization, over the molecular sieve at pressures of from 1 to 200 bar absolute, preferably at pressures of from 1 to 50 bar absolute, more preferably at temperatures of from 0° to 200° C., and most preferably at temperatures of from 20° to 160° C.

The direction of flow of the hydrocarbon feedstock mixture over the molecular sieve can be any direction, preferably upward.

In general, the protective effect afforded by the molecular sieve for the downstream oligomerization catalyst is long-lasting. If, however, a breakthrough of the catalyst poisons through the molecular sieve occurs after a certain period, a sure sign of such a breakthrough being a certain drop-off in the olefin conversion, it is possible to switch to a reserve molecular sieve and regenerate the exhausted sieve in the meantime.

The frequency at which the molecular sieve is regenerated depends inter alia on the size of the molecular sieve beds, the operating temperatures and the concentration of catalyst poison.

The molecular sieves can be regenerated in a conventional manner, for example, with an inert regeneration gas, such as nitrogen or hydrogen, or with a gaseous hydrocarbon such as methane or n-butane at temperatures of from about 160°-250° C.

Having now generally described this invention, a further understanding can be obtained by reference to certain specific examples which are provided herein for purposes of illustration only and are not intended to be limiting unless otherwise specified.

EXAMPLE 1

A 15% strength by weight solution of ethylene in n-butane is prepared. This solution is passed at room temperature over an adsorption bed comprising a molecular sieve having a pore diameter of 3 angstroms at an LHSV of 5 l of solution per l of adsorbent per hour, and thereafter the acetylene still present in traces is selectively hydrogenated over a catalyst based on 0.5% by weight of Pd on $Al_2O_3$ at a WHSV of 20 $h^{-1}$.

The solution thus pretreated is passed at a temperature of 25° C. and a pressure of 50 bar absolute over a molecular sieve of type 13 X from Bayer AG (pore diameter 9 angstrom) at a WHSV of 4 $h^{-1}$. Any catalyst poisons were below the limit of detection both upstream and downstream of the molecular sieve of type 13 X from Bayer AG. The solution thus prepared is oligomerized at a temperature of 70° C., a pressure of 50 bar and a WHSV of 4 $h^{-1}$ over a nickel-exchanged montmorillonite (montmorillonite from Fluka AG, preparation: J. R. Sohn, H. B. Park, J. kor. chem. Soc. 26(5), pp. 282, 1982). The ethylene conversion remains unchanged over a week at 99%.

COMPARATIVE EXAMPLE 1

The ethylene oligomerization is carried out as described in Example 1, except that the molecular sieve of type 13 X from Bayer is omitted. The ethylene conversion decreases by about 0.5% per day and is only 95.5% after a week.

EXAMPLE 2

Refinery propene containing about 75% by weight of propene and 0.45 ppm by weight of sulphur is pretreated and then oligomerized as described in Example 1, except that prior to oligomerization the refinery propene is passed over a copper-exchanged X-zeolite containing 4.5% by weight of Cu (pore diameter 8 angstroms prior to the exchange with copper) at a temperature of 120° C., a pressure of 50 bar absolute and a WHSV of 0.75 $h^{-1}$. After passing through this Cu-zeolite, the sulfur content of the refinery propene is only 7 ppb by weight. The oligomerization was carried out over a nickel-aluminum-silica catalyst comprising 15.3% by weight of NiO, 9.3% by weight of $Al_2O_3$ and 75.4% by weight of $SiO_2$, prepared as described in DE Patent 2,051,402 by coprecipitation of $Ni(NO_3)_2$ with sodium silicate in the presence of colloidal aluminum oxide. A WHSV of 5 $h^{-1}$, a pressure of 50 bar absolute and a temperature of 60° C. gives a propene conversion of 53.5% which is virtually still unchanged four weeks later at 53.0%.

COMPARATIVE EXAMPLE 2

Refinery propene is pretreated and oligomerized as in Example 2, except that the copper-exchanged X-zeolite is left out. At the end of a one-week run the propene conversion had dropped to 21.5%.

EXAMPLE 3

A $C_4$-hydrocarbon cut from an MTBE-plant, having an n-butenes content of 75% by weight, is distilled to remove isobutane therefrom. At the same time the distillation removes any residual moisture content and the entire methanol and dimethyl ether content overhead. The butene concentrate obtained as a bottom product, comprising 79% by weight of n-butene, 0.05% by weight of isobutene, 0.7 ppm by weight of tert-butyl alcohol and 1.1 ppm by weight of methyl tert-butyl ether, is selectively hydrogenated as described in Example 1, passed over a molecular sieve of type 13 X from Union Carbide (pore diameter 10 angstrom) at a temperature of 20° C., a pressure of 50 bar absolute and a WHSV of 6 $h^{-1}$, and then oligomerized at a temperature of 140° C., a pressure of 20 bar absolute and a WHSV of 6 0.1 /h. Downstream of the molecular sieve of type 13 X from Union Carbide, the level of tert-butyl alcohol is 40 ppb by weight and that of methyl tert-butyl ether is 90 ppb by weight.

The catalyst used for the oligomerization is prepared as follows:

A 500 g amount of a molecular sieve of type 13 X from Bayer AG is covered with 1 liter of 1M nickel nitrate solution and left at a temperature of 80° C. for 6 hours with occasional shaking. The solution is then decanted, and the catalyst is dried at a temperature of 120° C. for 5 hours and is then calcined at a temperature of 350° C. under nitrogen for 48 hours. The ready-produced oligomerization catalyst contains 9.7% by weight of nickel.

The butene conversion is 32%, following a running in period of 3 days, and remains unchanged over the next 14 days.

COMPARATIVE EXAMPLE 3

The oligomerization is carried out as described in Example 3, except that the molecular sieve of type 13 X from Union Carbide is replaced by a molecular sieve of type 4 A from Bayer AG (pore diameter 4 angstroms). Initially the butene conversion is the same, but after 14 days it has dropped to 20%.

EXAMPLE 4

A butadiene-free $C_4$-hydrocarbon mixture containing 83.9% by weight of n-butenes is admixed with 0.8 ppm by weight of dimethylamine. This hydrocarbon feedstock mixture is passed over a molecular sieve of type 5 A from Bayer AG (pore diameter 5 angstroms) at a temperature of 23° C., a pressure of 25 bar absolute and a WHSV of 2 $h^{-1}$ and thereafter contains only 60 ppb by weight of the added amine. This is followed by the oligomerization of the butene at a WHSV of 1 $h^{-1}$ at a temperature of 100° C. and a pressure of 25 bar absolute over the catalyst prepared as follows:

A 250 g amount of a Y-zeolite from Ventron, Karlsruhe is covered with 500 ml of 1M nickel nitrate solution and maintained at a temperature of 70° C. for 6 hours. The solution is then decanted off and discarded. The Y-zeolite thus treated is then extracted with hot water for 24 hours and calcined at a temperature of 350° C. under nitrogen for 24 hours. The ready-produced oligomerization catalyst contains 4.9% by weight of nickel.

The butene conversion is 29.4%, following a running-in period of three days, and is virtually unchanged after three weeks, at 29.0%.

COMPARATIVE EXAMPLE 4

The oligomerization as per Example 4 is repeated, except that the dimethylamine is not separated beforehand over the molecular sieve of type 5 A from Bayer AG. The butene conversion decreases continuously. After three days it is 27% and after a week only 12%.

EXAMPLE 5

A $C_8$-hydrocarbon fraction containing 99.5% by weight of octenes additionally contains 400 ppm by weight of polyunsaturated olefins and 1 ppm by weight of sulfur. It is selectively hydrogenated and then passed over a zinc-exchanged molecular sieve containing 2% by weight of zinc at a temperature of 20° C., a pressure of 50 bar absolute and a WHSV of 1 $h^{-1}$. The zinc-exchanged molecular sieve is obtained by ion exchange of the phyllosilicate of type K10 from Sudchemie (pore diameter 13 angstrom). The $C_8$-hydrocarbon fraction thus pretreated, which had no detectable polyunsaturated olefin content but still had a sulfur content of 43 ppb by weight, is oligomerized at a temperature of 100° C., a pressure of 5 bar absolute and a WHSV of 1 $h^{-1}$. The oligomerization catalyst used herein is prepared as described in Example 3, except that the catalyst is extracted with hot water for 24 hours prior to drying. The nickel content of the ready-produced oligomerization catalyst is 5.5% by weight.

Following a running-in period of 3 days, the octene conversion is 24% and is still unchanged three weeks later.

COMPARATIVE EXAMPLE 5

The oligomerization as per Example 5 is repeated, except that the $C_8$-hydrocarbon fraction is not passed beforehand over the zinc-exchanged molecular sieve. The butene conversion after three days is down to 17%, and after three weeks it has dropped to zero.

Having now fully described the invention, it will be apparent to one of ordinary skill in the art that many changes and modifications can be made thereto without departing from the spirit or scope of the invention as set forth herein.

We claim:

1. A process for oligomerizing olefins, comprising:
   passing a hydrocarbon feedstock mixture containing olefins of from 2 to 8 carbon atoms over a molecular sieve having a pore diameter of from greater than 4 angstroms to 15 angstroms, thereby removing catalyst poisons from the feedstock mixture;
   removing polyunsaturated hydrocarbons from the hydrocarbon feedstock mixture by selective hydrogenation either before or after passage of the hydrocarbon feedstock mixture over the molecular sieve; and then
   oligomerizing said olefins by passing the hydrocarbon feedstock over a nickel-containing catalyst at a temperature of from 0° to 200° C. and at a pressure of from 1 to 70 bar absolute.

2. The process according to claim 1, which further comprises:
   removing water, alcohols, nitrogen compounds, sulfur compounds and halogen compounds from the hydrocarbon feedstock mixture before it is passed over the molecular sieve having a pore diameter of from greater than 4 angstroms to 15 angstroms.

3. The process according to claim 2, wherein the materials removed from the feedstock prior to contact of the feedstock with the molecular sieve, are reduced in concentration down to about 1000 ppm.

4. The process according to claim 1 or 2, wherein the olefins in the hydrocarbon feedstock mixture are oligomerized over a heterogeneous nickel-containing catalyst.

5. The process according to claim 4, wherein the olefins in the hydrocarbon feedstock mixture are oligomerized over a nickel-, silicon- and aluminum-containing fixed-bed catalyst.

6. The process according to claim 1, wherein the olefins in the hydrocarbon feedstock mixture are oligomerized in the liquid phase.

7. The process according to claim 1, wherein the hydrocarbon feedstock mixture is passed, prior to the oligomerization, over the molecular sieve at pressures of from 1 to 200 bar absolute.

8. The process according to claim 1, wherein the hydrocarbon feedstock mixture is passed, prior to the oligomerization, over the molecular sieve at temperatures of from 0° to 200° C.

9. The process according to claim 1, wherein the polyunsaturated hydrocarbons are removed from the hydrocarbon feedstock mixture prior to the oligomerization.

10. The process according to claim 9, wherein the polyunsaturated hydrocarbons are removed from the hydrocarbon feedstock mixture by selective hydrogenation.

11. The process according to claim 10, wherein the polyunsaturated hydrocarbons are removed from the hydrocarbon feedstock mixture by selective hydrogenation down to a residual level of less than 5 ppm by weight.

12. The process according to claim 1, wherein the hydrocarbon feedstock passes over the molecular sieve at a weight hourly space velocity of 0.05 to 100 l/hr.

* * * * *